United States Patent [19]

Weisbart

[11] Patent Number: 4,812,397

[45] Date of Patent: Mar. 14, 1989

[54] MAB-ANTI-DNA RELATED TO NEPHRITIS

[75] Inventor: Richard H. Weisbart, Los Angeles, Calif.

[73] Assignee: The Regents of the University of California, Berkeley, Calif.

[21] Appl. No.: 12,830

[22] Filed: Feb. 10, 1987

[51] Int. Cl.$^4$ ................. G01N 33/00; G01N 33/53
[52] U.S. Cl. ..................................... 435/7; 436/501; 436/528; 436/530; 436/531; 436/538; 436/548; 436/811; 935/110
[58] Field of Search ............... 435/7; 436/501, 528, 436/530, 531, 538, 548, 811; 935/110

[56] References Cited

U.S. PATENT DOCUMENTS 3,897,212  7/1975  Leon et al. ................. 436/539 X
4,623,627  11/1986  Huang et al. ............... 530/387 X
4,690,905  9/1987  Diamond ..................... 436/538 X

OTHER PUBLICATIONS

Hahn, B. et al., "Suppression of Murine Lupus Nephritis . . . ", J. Immunology 132(1), 187–190 (Jan., 1984).

Primary Examiner—Robert J. Warden
Assistant Examiner—Richard Wagner
Attorney, Agent, or Firm—Bertram I. Rowland

[57] ABSTRACT

Novel compositions and methods are provided for detecting lupus nephritis in patients suffering from SLE. Competitive or non-competitive assays may be employed, where monoconal antibodies may be used to compete with antiserum for a nucleic acid ligand or may be used for the detection of antiidiotype antibodies as diagnostic of the presence or absence of lupus nephritis.

22 Claims, No Drawings

MAB-ANTI-DNA RELATED TO NEPHRITIS

TECHNICAL FIELD

Compositions and diagnostic assays are provided for detection of systemic lupus erythematosus and lupus nephritis.

BACKGROUND OF THE INVENTION

Antibodies to DNA are a prominent serological feature of systemic lupus erythematosus (SLE) and constitute a wide spectrum of specificities, including antibodies that bind only single-stranded deoxyribose nucleic acid (ssDNA), only native DNA (nDNA), and antibodies that bind both ssDNA and nDNA. Antibodies to ssDNA are not specific for SLE in comparison to anti-nDNA nDNA antibodies, which, however, occur rarely. In contrast, antibodies that bind both ssDNA and nDNA occur frequently, are relatively specific for SLE, and are associated with glomerulonephritis in some patients with SLE. There is substantial interest in determining the fine specificity of antibodies binding to nucleic acids, particularly antibodies diagnostic of SLE and lupus nephritis.

BRIEF DESCRIPTION OF THE RELEVANT LITERATURE

Tan, et al., *J. Clin. Invst.* (1966) 45:173-1740; Koffler, et al., *J. Exp. Med.* (1967) 126: 607-624; and Koffler, et al., *Ibid.* (1971) 134: 294-312 describe the nature of antibodies to nucleic acids in human serum. Andrzejewski, et al., *J. Immunol.* (1981) 126: 226-231; Jacob & Tron, *Ibid.* (1982) 128: 895-898; Marion, et al., *Ibid.* (1982) 128: 668-674; Schoenfeld, et al., *N. Engl. J. Med.* (1983) 308: 414-419; and Yoshida, et al., *J. Clin. Invest.* (1985) 76: 685-694 report their investigations concerning polyspecificity idiotypic cross-reactivity of anti-DNA monoclonal antibodies.

SUMMARY OF THE INVENTION

Novel compositions are provided which find use in diagnostic assays for detection of human SLE and lupus nephritis. The monoclonal antibodies are used in assays with sera of suspected SLE patients as diagnostic of SLE and/or lupus nephritis. Indicative of the presence of SLE and absence of nephritis is the presence of antiidiotype sera for subject antibodies.

DESCRIPTION OF SPECIFIC EMBODIMENTS

Novel monoclonal antibodies are provided which are characterized by binding to both single-stranded DNA (ssDNA) and native DNA (nDNA). The subject antibodies bind substantially equally well to both ssDNA and nDNA, while poly-dT inhibits binding to ssDNA, but not the other poly-dNs, -dA, -dC, -dG, nDNA or poly-(dA, dT). Poly-dI inhibits binding of the subject antibodies to ssDNA. The subject antibodies have little or no binding to RNA or cardiolipin. These antibodies are referred to as poly-dT specific antibodies.

The subject of poly-dT specific monoclonal antibodies may be used or their equivalent. The monoclonal antibodies may be any of the classes or subclasses, including IgA, IgD, IgE, IgG (subclasses 1-4, if human; 1, 2a, 2b, 3 if murine) or IgM. Actively binding fragments of the antibodies may be employed, such as Fab, Fv, F(ab')$_2$, or the like. The monoclonal antibodies may be prepared by any convenient means which provides immortalization of the B-lymphocyte genes expressing the antibody subunits or Fv, such as fusion between sensitized lymphocytes and a myeloid fusion partner, transformation, e.g., with EBV, or other immortalization technique. Alternatively, the genes can be isolated from a lymphocytic host expressing the antibodies and transferred to a more convenient host for expression in accordance with known genetic engineering techniques. Finally, if desired, naturally occurring antisera of SLE patients may be employed and the desired antibodies isolated employing affinity chromatography.

The antibodies may be obtained from any convenient vertebrate source, such as murine, primate, e.g. human, lagomorpha, bovine, ovine, equine, porcine, etc.

The antibodies may be prepared by fusing spleen cells from a host having elevated serum levels of anti-DNA antibodies with myeloma cells in accordance with known techniques or by transforming the spleen cells with an appropriate transforming vector to immortalize the cells. The cells may be cultured in a selective medium and screened to select antibodies that bind both nDNA and ssDNA and are poly-dT specific.

For diagnostic assays, the antibodies may be used without modification or may be labeled depending upon the particular protocol that is employed. A wide variety of labels are known which provide for a detectable signal. Illustrative labels include radioisotopes, e.g., $^3$H, $^{125}$I, $^{131}$I, $^{14}$C; fluorescers, e.g., fluorescein, phycobiliproteins, rare earth chelates, rhodamine, etc.; enzyme substrates and inhibitors; enzymes, such as horseradish peroxidase, glucose oxidase, glucose-6-phosphate dehydrogenase, $\beta$-galactosidase, acetylcholinesterase, etc.; particles, e.g., dextran, agarose, metal particles, carbon, magnetic particles, polystyrene particles, etc., or the like. Methods for conjugating labels to proteins have found extensive description in the literature, see, for example, U.S. Pat. Nos. 3,817,837; 4,134,792; and 4,220,722.

The labeling employed will follow conventional techniques and the number of labels per antibody will vary depending upon the nature of the label, the sensitivity of the signal desired, the purpose of the labeling and the like. Numerous assay protocols have been developed for use with antibodies for the detection of a wide variety of analytes which are applicable here. See, for example, U.S. Pat. Nos. 3,791,932; 3,817,837; 4,134,792; 4,174,384; 4,275,149; and 4,299,916, which are incorporated herein by reference.

The subject antibodies are used in competitive assays, where determination is based upon the amount of the subject antibodies which are precluded from binding to a nucleic acid ligand. For the purpose of the subject invention, the ligand may be ssDNA, nDNA or poly-dT, particularly poly-dT, where ssDNA, nDNA, and/or poly-dT may serve as ligands in the competitive assay, individually or combined. Finding a positive result, namely competitive antibodies in the antisera of a patient, will be indicative of the presence of lupus nephritis.

A second aspect of the subject invention is the determination of the presence of antiidiotypic anti-DNA antibodies which bind to the subject antibodies. In this case, one is solely interested in the presence of antibodies which bind to the subject antibodies or their immunological equivalent and the assays will vary from the competitive assay. As immunological equivalents, Fv, Fab, F(ab')$_2$, oligopeptides, or the like having an epitope competitive with the idiotype (idiotope or paratope) may be employed. Conveniently, the subject antibodies may be bound to a solid support, contacted with the blood sample, which may have been subject to prior treatment, e.g., removal of cells, followed by contacting with labeled antibodies which bind to human antibodies. In this instance, the antibodies of the subject invention will be other than human antibodies. The specific binding of the labeled antihuman immunoglobulin to the support will be indicative of the presence of the antiidiotypic anti-DNA antibodies. The presence of these antibodies are diagnostic for SLE and indicative of the absence of lupus nephritis.

In carrying out the subject assays, it will normally be desirable to determine initially if the antiidiotypic anti-DNA antibodies are present, since their presence could inhibit the binding of the subject antibodies to a nucleic acid ligand, falsely indicating the presence of competitive antibodies. If the antiidiotypic anti-DNA antibodies are found to be present, they may be removed by any convenient means, e.g., affinity chromotography, separation with particles coated with the subject antibodies, followed by centrifugation, or the like. The resulting serum free of antiidiotypic anti-DNA antibodies may then be used for determination of the presence of competitive antibodies.

The following examples are offered by way of illustration and not by way of limitation.

EXPERIMENTAL

Patients

Serum was obtained from 286 subjects including 106 with SLE diagnosed by revised American Rheumatism Association criteria (Tan, et al., *Arthritis Rheum.* (1982) 25: 1271-1277). Glomerulonephritis was diagnosed in 35 SLE patients by two or more of the following: diagnostic histopathology of renal biopsy, proteinuria>1.0 gm/day, urinary cellular casts, diminished renal function with elevated serum creatinine or diminished creatinine clearance. Serum was also obtained from control subjects including 18 with systemic sclerosis (SS), 96 with rheumatoid arthritis (RA), 30 with ankylosing spondylitis (AS), 6 with degenerative joint disease (DJD), and 30 healthy subjects.

Monoclonal antibodies

Monoclonal anti-DNA antibodies were obtained by fusing spleen cells from MRL/1pr mice with the FOX-NY myeloma cell line as previously described (Taggart and Samloff, *Science* (1983); 219:1228-1230) Weisbart, et al., *J. Immunol.*, (1984) 132: 2909-2912). Briefly, spleen cells ($2.4 \times 10^8$) from MRL/1pr mice (Jackson Laboratories, Bar Harbor, Me.) with elevated serum levels of anti-DNA antibodies were fused with $4.8 \times 10^7$ myeloma cells using 50% polyethylene glycol 1600. The cells were cultured at $1 \times 10^6$/ml in 96-well plates in 0.2 ml RPMI 1640 and 10% fetal calf serum. Culture supernatants were harvested after 10 days and assayed for IgG antibodies to ssDNA and nDNA by enzyme-linked immunosorbent assay (ELISA) as previously described (Weisbart, et al., *Annals Int. Medicine* (1986) 104: 310-313). Screening was designed to select only IgG antibodies that bound both nDNA and ssDNA, and antibodies were excluded that bound bovine albumin or poly-L-lysine. Three antibodies designated 3E10, 5C5, and 5C6 were selected and cloned by limiting dilution. Murine IgG subclasses were determined by ELISA with goat subclass specific antisera. The specificity of binding of MAbs to DNA was determined by competitive inhibition of binding ssDNA in the presence of soluble DNA and various nucleotides and polynucleotides at a concentration of 50 μg/ml. MAbs were assayed at dilutions (0.5–10 μg/ml) that gave comparable responses by ELISA. Cloned cells ($10^7$) producing 3E10 were injected into the peritoneal cavities of pristane-primed Balb/c mice, and 3E10 was purified from ascites by binding to protein-A sepharose and removing non-immunoglobulin proteins by washing with 0.5M NaCl in phosphate buffer, pH 7.2, followed by 0.1M tris-glycine HCl, pH 4.0. 3E10 was eluted from protein-A with 0.1M tris-glycine HCl, pH 2.8. MAb 3E10 was identified as a single heavy and light chain band by sodium dodecyl sulfate polyacrylamide gel electrophoresis (SDS-PAGE).

Anti-DNA antibodies

Human serum and murine monoclonal antibodies to calf thymus ssDNA and nDNA (Sigma Chemical Co., St. Louis, Mo.) were measured by ELISA by coating 96-well plastic dishes with poly-L-lysine followed by incubation with DNA (Weisbart, et al., (1986) supra. DNA was denatured (ssDNA) by heating to 100° C. followed by rapid cooling. The wells were washed and incubated overnight with 100 μl of mouse or human serum diluted 1:100. The wells were washed with phosphate buffered saline, pH 7.4, containing 0.1% Tween 20 (PBST), and serum IgG bound to the dish was detected with alkaline phosphatase-conjugated goat antiserum specific for mouse or human IgG (Cooper Biomedical, Inc., Malver, Penn.). The IgG response to DNA was measured as the difference between the binding on DNA on poly-L-lysine and poly-L-lysine alone. Human antibodies similar in specificity to murine MAbs were measured by inhibiting the binding of MAbs at concentrations of 0.5–10 μg/ml to nDNA or ssDNA in the presence of human serum diluted 1:100. The data were expressed as percent inhibition of MAb binding DNA. Inhibition was considered positive if greater than 20%, corresponding to more than 2 standard deviations above the mean response of control sera from healthy subjects. Sera with antibodies to 3E10 that also inhibited binding of 3E10 to nDNA were adsorbed with purified 3E10 bound to plastic dishes until all 3E10 binding activity was removed. The adsorbed sera were then reassayed for inhibition of binding of 3E10 to nDNA.

Antiidotypic antibodies

Purified 3E10 was bound to 96-well plastic dishes to assess binding of human serum IgG to 3E10. To detect antiidiotypes selective for the 3E10 idiotype, anti-3E10 binding was assayed in the presence of excess (50 μg/ml) soluble MAb 5C5. Antiidiotypic antibodies were quantitated by a standard curve for human IgG; goat antibodies specific for human IgG were bound to plastic wells, and known amounts of human IgG were added and incubated overnight. Human IgG was detected with goat anti-human IgG conjugated with alkaline phosphatase. Antiidiotype specificity was determined by inhibiting the binding of human IgG to 3E10 with soluble ssDNA, nDNA, and various polynucleotides at a concentration of 50 μg/ml, and the results expressed as percent inhibition of the IgG response to 3E10. Human IgG that bound 3E10 and was inhibited by excess soluble nDNA was measured as μg/ml of serum.

Isolation of serum anti-DNA and antiidiotypic anti-DNA antibodies

Serum factors that inhibited binding of 3E10 to nDNA were isolated from SLE sera and identified as IgG by binding to and elution from protein-A sepharose. Human serum, 0.1 ml, was incubated with protein-A sepharose for 30 minutes with continuous mixing. The beads were centrifuged and washed with 0.15M phosphate-buffered saline, pH 7.4 (PBS). Adsorbed sera were assayed for inhibiting binding of 3E10 to nDNA. The protein-A sepharose beads were eluted with 0.1M tris-glycine HCl, pH 2.8, by continuous mixing for 5 minutes followed by centrifugation for 5 minutes at 400×g. Eluates were immediately removed from the beads and rapidly neutralized with 0.1M sodium carbonate buffer to pH 7.4. Eluted fractions were assayed simultaneously with adsorbed fractions for inhibition of binding of 3E10 to DNA.

Depletion of serum antibodies to nDNA and 3E10

Sera were depleted of specific antibodies by solid phase adsorption as previously described (Yee and Weisbart, Clinical Immunology and Immunopathology (1985) 36: 161–167. Briefly, nDNA (15 µg/ml in tris-HCl) was added to 96-well plastic dishes coated with poly-L-lysine, and purified 3E10 (15 µg/ml) was bound to plastic in 0.06M sodium carbonate, pH 9.6. Sera diluted 1:50 were passed through 8 wells for 2 hours each, including an overnight incubation. The sera were assayed after adsorption for binding to DNA, and if positive, were readsorbed until negative at a dilution of 1:100.

Characterization of MAbs

Antibodies 3E10, 5C5, and 5C6 were all identified as IgG 2a by isotype specific antisera and were purified by protein-A to apparent homogeneity as determined by SDS-Page. The binding specificities of the three MAbs were quite different as shown by inhibition of binding to ssDNA in the presence of various polynucleotides (Table 1). Dose-dependent inhibition of binding was demonstrated at 50 µg/ml of inhibitor as shown in Table 1.

TABLE 1
Monoclonal Antibody Specificity

| Inhibitor (50 µg/ml) | % Inhibition of Binding of MAb to ssDNA | | |
|---|---|---|---|
| | 3E10 | 5C5 | 5C6 |
| nDNA | 44 | 23 | 38 |
| ssDNA | 50 | 83 | 71 |
| poly-dA | 0 | 0 | 0 |
| poly-dC | 1 | 0 | 0 |
| poly-dG | 4 | 0 | 0 |
| poly-dT | 88 | 0 | 10 |
| poly-dI | 56 | 34 | 29 |
| poly-(dA,dt) | 0 | 56 | 8 |
| 10174 DNA | 34 | 36 | 44 |
| RNA | 12 | 10 | 3 |
| AMP | 0 | 0 | 1 |
| CMP | 4 | 0 | 0 |
| GMP | 1 | 0 | 0 |
| TMP | 2 | 0 | 0 |

The binding of 3E10 to ssDNA was equally inhibited by ssDNA and nDNA in contrast to 5C5 and 5C6 which showed greater binding to ssDNA than to nDNA. The restricted specificity of 3E10 was indicated by its inhibition of binding to ssDNA by poly-dT but no poly-dA, poly-dC, poly-dG, or poly-(dA, dT). In contrast, 5C5 and 5C6 were not significantly inhibited by poly-dT. Moreover, only 5C5 was inhibited by poly-(dA, dT). Poly-dI inhibited binding of each of the MAbs to DNA. None of the MAbs bound individual mononucleotides. Each of the MAbs bound phage DNA as well as calf thymus DNA, but there was minimal binding to RNA emphasizing the contribution of deoxyribose to the antigenic determinant. Binding of MAbs to nDNA independent of DNA-associated protein was confirmed with purified plasmid nDNA free of measurable protein. None of the three MAbs bound cardiolipin.

SLE serum inhibits binding of MAbs to DNA

The association of each murine MAb with human SLE was examined in preliminary experiments by inhibiting the binding of the MAbs to DNA in the presence of serum from SLE and control subjects. The MAbs were diluted to give comparable responses to DNA. Each of the three MAbs showed some specificity for SLE and nephritis, but 3E10 was more sensitive than 5C5 or 5C6 for detecting anti-DNA antibodies in SLE sera.

TABLE 2

| % Inhibition of MAb Binding ssDNA by Human Sera | | | |
|---|---|---|---|
| Patent Serum | 3E10 | 5C5 | 5C6 |
| SLE nephritis | | | |
| 1 | 66* | 43 | 43 |
| 2 | 30 | 11 | 13 |
| 3 | 24 | 10 | 19 |
| 4 | 52 | 28 | 31 |
| 5 | 50 | 18 | 24 |
| 6 | 73 | 44 | 4 |
| 7 | 24 | 15 | 16 |
| 8 | 56 | 33 | 36 |
| 9 | 33 | 14 | 10 |
| 10 | 0 | 8 | 4 |
| 11 | 16 | 6 | 15 |
| 12 | 11 | 20 | 16 |
| 13 | 20 | 9 | 8 |
| SLE without nephritis | | | |
| total 9       mean | 5 | 7 | 4 |
| Systemic Sclerosis | | | |
| total 7       mean | 2 | 7 | 5 |
| Rheumatoid Arthritis | | | |
| total 10      mean | 4 | 9 | 4 |
| Healthy | | | |
| total 10      mean | 2 | 1 | 1 |

*Positives, underlined (>2 S.D. above mean for controls).

The mean responses are shown for 9 SLE patients without nephritis and 27 non-SLE subjects, none of whom gave a positive response. MAb 3E10 was employed for the studies. Sera from three patients were studied to identify the factor(s) inhibiting binding of 3E10 to DNA. Serum IgG appeared to be responsible, because the inhibitory effect was completely removed after adsorbing serum with immobilized protein-A. Moreover, 96% of the inhibitory activity was recovered by eluting the protein-A with tris-glycine HCl, pH 2.8.

SLE serum Anti-DNA antibodies and antiidiotypic antibodies to 3E10 inhibit binding of 3E10 to nDNA Three sera that inhibited binding of 3E10 to nDNA contained anti-nDNA antibodies but not antibodies reactive with 3E10. To determine if anti-nDNA antibodies were responsible for inhibiting binding of 3E10 to nDNA, sera were adsorbed with nDNA bound to plastic dishes and reassayed for inhibition of 3E10. After adsorption with nDNA, the sera were depleted (greater than 90%) of IgG binding to nDNA at a dilution of 1:100. After adsorption with nDNA, the sera were no longer able to inhibit binding of 3E10 to nDNA (Table 3). In contrast, three other sera inhibited binding of 3E10 to nDNA, but did not have measurable antibodies to nDNA. In each case, these sera were found to contain IgG antibodies that bound 3E10 (antiidiotypes).

To determine if antibodies to 3E10 rather than anti-nDNA antibodies inhibited binding of 3E10 to nDNA, the three sera were adsorbed with nDNA bound to plastic dishes and reassayed for inhibitory activity. Adsorbing these sera with nDNA did not inhibit binding of 3E10 to nDNA.

Adsorbing these sera with 3E10 did, however, remove more than 90% of the inhibitory activity. These results show the presence of human anti-nDNA antibodies similar to 3E10 that inhibit its binding to nDNA. In addition, the results show that some sera contain antibodies to 3E10 that inhibit binding of 3E10 to nDNA.

TABLE 3

SLE Serum anti-DNA (idiotypes) and anti-3E10 (antiidiotypes) Inhibit Binding of 3E10 to nDNA

| Pt.+ | SLE Nephritis | % CI* 3E10 by serum | % CI* 3E10 after adsorbed with nDNA | 3E10 anti-id ($\mu$g/ml) | anti-nDNA (O.D.)** |
|---|---|---|---|---|---|
| 1 | yes | 31 | 0 | 0 | 0.42 |
| 2 | yes | 34 | 11 | 0 | 0.40 |
| 3 | yes | 22 | 0 | 0 | 1.40 |
| 4 | no | 29 | 20 | 18 | 0.00 |
| 5 | no | 30 | 26 | 20 | 0.00 |
| 6 | no | 28 | 28 | 15 | 0.00 |

*CI = competitive inhibition.
+Pt = patient
**O.D. = optical density

The fine specificity of 3E10 antiidiotypes in SLE sera and relation to idiotype expression Serum from 286 subjects was assayed for IgG antibodies to 3E10, including 106 SLE patients, 18 with systemic sclerosis, 96 with rheumatoid arthritis, 30 with ankylosing spondylitis, 6 with degenerative joint disease, and 30 healthy subjects. Antiidiotypic antibodies were detected by measuring only the antibody response to 3E10 that could be blocked by the presence of excess (50 $\mu$g/ml) soluble nDNA. Serum from only 17 patients had measurable antiidiotypic antibodies to 3E10, 16 with SLE, and one patient with rheumatoid arthritis. The fine specificity of the antiidiotypes was assessed by inhibiting binding of serum IgG to 3E10 with various polynucleotides. Poly-dT was the most consistent inhibitor of binding, and showed more than 30% inhibition in 12 of the 16 SLE patients.

TABLE 4

Polynucleotide Specificity of SLE Serum Antiidiotypic Antibodies to 3E10 and Relation to Idiotype Expression

| | SLE Neph*/Active | 3E10 Id % CI+ | Anti-3E10 ($\mu$g/ml) | % Inhibition Anti-3E10 by Polynucleotides | | | |
|---|---|---|---|---|---|---|---|
| | | | | dT | dA | dC | dG |
| 1 | yes/yes | 43 | 43 | 0 | 3 | 0 | 0 |
| 2 | yes/yes | 35 | 36 | 5 | 30 | 3 | 16 |
| 3 | yes/yes | 33 | 38 | 18 | 28 | 14 | 20 |
| 4 | yes/no | 49 | 28 | 18 | 29 | 7 | 9 |
| 5 | yes/yes | 0 | 16 | 76 | 12 | 0 | 15 |
| 6 | yes/no | 0 | 22 | 60 | 12 | 5 | 7 |
| 7 | yes/no | 0 | 18 | 49 | 23 | 11 | 29 |
| 8 | yes/no | 0 | 16 | 87 | 0 | 0 | 6 |
| 9 | yes/no | 0 | 24 | 60 | 15 | 0 | 11 |
| 10 | yes/no | 0 | 16 | 82 | 15 | 12 | 30 |
| 11 | no | 0 | 14 | 59 | 33 | 0 | 22 |
| 12 | no | 0 | 18 | 25 | 0 | 0 | 0 |
| 13 | no | 0 | 18 | 54 | 11 | 0 | 0 |
| 14 | no | 0 | 9 | 53 | 0 | 0 | 0 |
| 15 | no | 0 | 15 | 67 | 43 | 27 | 37 |
| 16 | no | 0 | 12 | 76 | 56 | 32 | 28 |

*Neph = Nephritis.
+CI = Competitive inhibition of 3E10 binding nDNA by human serum adsorbed with 3E10 and diluted 1:100.

Only one of these patients had active nephritis, consistent with mild focal disease, even though 35/106 SLE patients (33%) had nephritis. Moreover, none of these patients expressed the 3E10 idiotype. Of the four remaining SLE patients, three had diffuse proliferative glomerulonephritis, and all four patients had antiidiotypic antibodies to 3E10 which were inhibited by nDNA but not (less than 20%) by poly-dT. Furthermore, all of these patients expressed the 3E10 idiotype. Inhibition of antiidiotype binding to 3E10 occurred less frequently with the other polynucleotides.

Association of the 3E10 idiotype with lupus nephritis

Human serum anti-nDNA antibodies similar to monoclonal 3E10 from MRL/1pr mice with SLE were measured by inhibiting the binding of 3E10 to nDNA. To eliminate the contribution of antiidiotypes in this assay, all sera with IgG that bound 3E10 were adsorbed with immobilized, purified 3E10 until they assayed negatively for binding 3E10 at a dilution of 1:100. The adsorbed sera were then assayed for inhibition of binding of 3E10 to nDNA. Serum from 17 of 35 patients with SLE and nephritis inhibited binding of 3E10 to nDNA by 20% or more, whereas only 6 of 71 sera from SLE patients without nephritis showed this inhibitory activity ($X^2 = 19.91$, $p > 0.0001$). The mean inhibition response of the 17 SLE patients with nephritis was 30%, and the mean inhibition response of the 6 SLE patients without nephritis was 38%. In contrast, the mean inhibition response of the 180 non-SLE subjects was only 2%. Furthermore, none of the 180 sera from patients without SLE inhibited the binding of 3E10 to nDNA, emphasizing the specificity of the 3E10 idiotype for SLE.

TABLE 5

Association of 3E10 Idiotype with Lupus Nephritis

| | No. Pts. | 3E10 Idiotype No. Positive | Anti-nDNA No. Positive |
|---|---|---|---|
| SLE Nephritis | 35 | 17* | 24+ |
| No Nephritis | 71 | 6 | 25 |
| total | 106 | | |
| SS | 18 | 0 | 1 |
| RA | 96 | 0 | 1 |
| AS | 30 | 0 | 0 |
| DJD | 6 | 0 | 0 |
| Healthy | 30 | 0 | 0 |
| total | 180 | | |

*$X^2 = 19.21$, $p < 0.00001$ for association of 3E10 idiotype with lupus nephritis.
+$X^2 = 9.20$, $p < 0.01$ for association of anti-nDNA with lupus nephritis.
SLE, systemic lupus erythematosus; SS, systemic sclerosis; RA, rheumatoid arthritis; AS, ankylosing spondylitis; DJD, degenerative joint disease.

The data confirm the association of anti-nDNA antibodies with lupus nephritis ($X^2 = 9.20$, $p < 0.01$). Responses greater than 0.25 were considered positive since they were more than 2 S.D. above the mean for the 30 healthy subjects. The mean anti-nDNA response $\pm$ SEM (O.D.) of the 24 SLE patients with nephritis was $1.00 \pm 0.11$, and the mean response of the 25 SLE patients without nephritis was $0.70 \pm 0.09$. In addition, one RA and one SS patient had antibodies to nDNA with responses (O.D.) of 0.78 and 0.88, respectively. Although the 3E10 idiotype was less sensitive than anti-nDNA antibodies for lupus nephritis, (49% vs. 69%, respectively), the 3E10 idiotype was more specific than anti-nDNA antibodies for lupus nephritis (92% vs. 65%, respectively). The positive predictive value of the 3E10 idiotype for SLE nephritis was 76%, and the negative predictive value was 75% based on a prevalence rate of 33% for nephritis in SLE.

It is evident from the above results that the subject compositions provide for a sensitive assay for lupus nephritis, where the compositions may be used by themselves or in combination with anti-nDNA for confirmatory detection of lupus nephritis. In this manner, the nephritis condition may be detected and treated, where the condition might otherwise be allowed to degenerate further.

Although the foregoing invention has been described in some detail by way of illustration and example for purposes of clarity of understanding, it will be obvious that certain changes and modifications may be practiced within the scope of the appended claims.

What is claimed is:

1. A method for diagnosing one of systemic lupus nephritis or lupus erythematosus, said method comprising:
   determining the presence in a blood sample of antibody capable of competing with an antibody composition having the following characteristics: specifically binding to all of the ligands poly-dT, ssDNA and nDNA; poly-dT and poly-dI inhibit binding of said antibody composition to ssDNA while the other poly-dNs do not inhibit binding of said antibody composition to ssDNA; said competition with said blood sample antibody being for at least one of said ligands; or
   determining the presence of antibody in said blood sample which binds the idiotype of said antibody composition;
   wherein the presence of competing antibody is indicative of lupus nephritis and the presence of idiotype binding antibody is indicative of systemic lupus erythematosus and contraindicative of lupus nephritis.

2. A method according to claim 1, wherein said competition is for poly-dT.

3. A method for diagnosing lupus nephritis employing an antibody composition having the following characteristics: specifically binding to all of the ligands poly-dT, ssDNA, and nDNA; poly-dT and poly-dI inhibit binding of said antibody composition to ssDNA while the other poly-dNs do not inhibit binding of said antibody composition to ssDNA; said method comprising:
   combining a blood sample with said antibody composition and at least one of said ligands to form an assay composition; and
   determining the amount of said antibody composition which binds to said ligands in comparison to the amount which binds in absence of said blood sample, wherein a reduced amount of binding is indicative of lupus nephritis.

4. A method according to claim 3, wherein said ligands in said assay composition are at least one of ssDNA and nDNA.

5. A method according to claim 3, wherein said ligands in said assay composition comprise at least poly-dT.

6. A method according to claim 3, wherein said determining is by means of a label bound to antibodies in said antibody composition.

7. A method according to claim 6, wherein said label is covalently bound to said antibodies.

8. A method according to claim 6, wherein said label is non-covalently bound to said antibodies by means of a labeled protein which binds to said antibodies.

9. A method according to claim 6, wherein said label is an enzyme, fluorescer or radioisotope.

10. A method according to claim 3, wherein said antibody composition is the monoclonal antibody 3E10.

11. A method for diagnosing systemic lupus erythrematosus and the probable absence of lupus nephritis employing an antibody composition having the following characteristics: specifically binding to all of the ligands poly-dT, ssDNA and nDNA; poly-dT and poly-dI inhibit binding of said antibody composition to ssDNA while the other poly-dNs do not inhibit binding of said antibody composition to ssDNA, or binding to an epitope comprising compound capable of competing with the idiotope of said antibody composition, said method comprising:
   combining a blood sample with said antibody composition; and
   determining the presence of antibodies which bind specifically to said antibody composition as an indication of systemic lupus erythrematosus and the probable absence of lupus nephritis.

12. A method according to claim 11, wherein said antibody composition is bound to a solid support.

13. A method according to claim 11, wherein said antibody composition is a murine antibody composition.

14. A method according to claim 11, wherein said determining is with a labeled antibody specific for human immunoglobulin.

15. A method according to claim 14, wherein said label is an enzyme, fluorescer or radioisotope.

16. A monoclonal antibody having the following characteristics: specifically binding to all of the ligands poly-dT, ssDNA and nDNA; poly-dT and poly-dI inhibit binding of said antibody composition to ssDNA while the other polydNs do not inhibit binding of said antibody composition to ssDNA.

17. A monoclonal antibody according to claim 16 of the class IgG and murine.

18. A monoclonal antibody according to claim 17 which is 3E10.

19. A monoclonal antibody according to claim 16 covalently bonded to a label providing a detectable signal.

20. A fragment with binding specificity of a monoclonal antibody according to claim 16.

21. A hybridoma secreting a monoclonal antibody having the following characteristics: specifically binding to all of the ligands poly-dT, ssDNA and nDNA; poly-dT and poly-dI inhibit binding of said antibody composition to ssDNA while the other poly-dNs do not inhibit binding of said antibody composition to ssDNA.

22. A hybridoma according to claim 21, wherein said antibody is 3E10.

* * * * *